(12) United States Patent
Di Ubaldi et al.

(10) Patent No.: US 10,857,343 B2
(45) Date of Patent: Dec. 8, 2020

(54) MEDICAL DEVICES WITH VISUAL AND TACTILE INDICATORS

(71) Applicant: Becton, Dickinson and Company, Franklin Lakes, NJ (US)

(72) Inventors: John Di Ubaldi, Jackson, NJ (US); Thirumurugan Nagu, Ramanathapuram (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 375 days.

(21) Appl. No.: 15/480,903

(22) Filed: Apr. 6, 2017

(65) Prior Publication Data

US 2018/0289941 A1 Oct. 11, 2018

(51) Int. Cl.
*A61M 39/10* (2006.01)
*A61M 5/178* (2006.01)
*A61M 5/31* (2006.01)

(52) U.S. Cl.
CPC ............ *A61M 39/10* (2013.01); *A61M 5/178* (2013.01); *A61M 5/3134* (2013.01); *A61M 39/1011* (2013.01); *A61M 2039/1044* (2013.01); *A61M 2039/1077* (2013.01); *A61M 2205/276* (2013.01); *A61M 2205/582* (2013.01); *A61M 2205/583* (2013.01); *A61M 2207/00* (2013.01)

(58) Field of Classification Search
CPC .............. A61M 39/10; A61M 39/1011; A61M 2039/1094; A61M 2039/1044; A61M 2039/1077; A61M 5/3134; A61M 2205/582; A61M 2205/583; A61M 2039/1033; A61M 5/34; A61M 25/0014; A61M 5/345–348
See application file for complete search history.

(56) References Cited

U.S. PATENT DOCUMENTS

| | | | |
|---|---|---|---|
| 5,041,097 A * | 8/1991 | Johnson | A61M 39/0606 604/167.02 |
| D327,318 S | 6/1992 | Dudar | |
| D395,502 S | 6/1998 | Deily | |
| 5,855,568 A * | 1/1999 | Battiato | A61M 5/14546 604/240 |
| 5,858,008 A | 1/1999 | Capaccio | |
| 5,865,818 A | 2/1999 | Gould | |
| 6,017,331 A | 1/2000 | Watts | |
| 6,494,865 B1 | 12/2002 | Alchas | |
| 6,508,807 B1 | 1/2003 | Peters | |
| 6,511,472 B1 | 1/2003 | Hayman | |
| D471,272 S | 3/2003 | Douglas | |

(Continued)

FOREIGN PATENT DOCUMENTS

WO 2004037335 A1 5/2004

OTHER PUBLICATIONS

PCT International Search Report and Written Opinion in PCT/US2018/026249 dated Jul. 25, 2018, 14 pages.

(Continued)

*Primary Examiner* — Bhisma Mehta
*Assistant Examiner* — James D Ponton
(74) *Attorney, Agent, or Firm* — Servilla Whitney LLC (57) ABSTRACT

Connectors for medical devices include visual and tactile features as an indicator of a connection-type of the connector. This allows for differentiation by type of connection under busy and/or low light conditions.

22 Claims, 6 Drawing Sheets

(56) References Cited

U.S. PATENT DOCUMENTS

| | | |
|---|---|---|
| D474,839 S | 5/2003 | Francavilla |
| D484,241 S | 12/2003 | Peters |
| 6,702,769 B1 | 3/2004 | Owens |
| 6,722,705 B2 | 4/2004 | Korkor |
| D493,526 S | 7/2004 | Hwang |
| D586,472 S | 2/2009 | Harold et al. |
| D591,438 S | 4/2009 | Hama |
| D654,166 S | 2/2012 | Lair |
| D668,760 S | 10/2012 | Kawamura |
| 8,652,094 B2 | 2/2014 | David et al. |
| 8,672,883 B2 | 3/2014 | Denning et al. |
| 8,814,849 B1 | 8/2014 | Winsor |
| D714,935 S | 10/2014 | Nishioka |
| 8,968,271 B2 | 3/2015 | Guala |
| D731,647 S | 6/2015 | Nishioka |
| D736,914 S | 8/2015 | Schultz |
| D736,915 S | 8/2015 | Schultz |
| D737,961 S | 9/2015 | Schultz |
| D737,962 S | 9/2015 | Schultz |
| D740,412 S | 10/2015 | Strong |
| D750,775 S | 3/2016 | Carrel et al. |
| D751,699 S | 3/2016 | Mills |
| 9,433,768 B2 | 9/2016 | Tekeste et al. |
| D782,654 S | 3/2017 | Booth |
| D785,781 S | 5/2017 | Chan |
| D799,032 S | 10/2017 | Becker et al. |
| 2002/0115984 A1 | 8/2002 | Guala |
| 2002/0133124 A1 | 9/2002 | Leinsing et al. |
| 2002/0143297 A1 | 10/2002 | Francavilla |
| 2004/0225258 A1* | 11/2004 | Balestracci ......... A61M 5/3134 604/111 |
| 2005/0124970 A1 | 6/2005 | Kunin et al. |
| 2006/0271015 A1* | 11/2006 | Mantell ............... A61M 13/003 604/533 |
| 2007/0010796 A1 | 1/2007 | Moran |
| 2007/0066965 A1 | 3/2007 | Coambs |
| 2009/0099552 A1* | 4/2009 | Levy .................... A61M 39/10 604/533 |
| 2010/0249650 A1 | 9/2010 | Hikawa |
| 2012/0150129 A1* | 6/2012 | Jin ........................ A61M 39/10 604/240 |
| 2012/0175806 A1 | 7/2012 | Delano |
| 2013/0030387 A1* | 1/2013 | Williams ........... A61M 39/1011 604/256 |
| 2014/0276215 A1 | 9/2014 | Nelson |
| 2014/0276649 A1 | 9/2014 | Ivosevic |
| 2016/0175201 A1* | 6/2016 | Schuessler ............. F16L 15/08 604/516 |
| 2016/0250415 A1 | 9/2016 | Yagi |
| 2016/0339184 A1* | 11/2016 | Tekeste ............... A61M 5/3134 |

OTHER PUBLICATIONS

Non-Final Office Action in U.S. Appl. No. 29/599,771 dated Feb. 8, 2018, 15 pages.

Non-Final Office Action in U.S. Appl. No. 29/599,772 dated Feb. 8, 2018, 15 pages.

* cited by examiner

MEDICAL DEVICES WITH VISUAL AND TACTILE INDICATORS

TECHNICAL FIELD

The present disclosure relates to medical devices having visual and tactile indicators. In particular, medical devices such as syringes, which are engagable with needle hubs, filters, adapters and the like, have one or more features on an external surface that provide visual and tactile indications of the type of connection that is internal to a component of the syringe, for example a slip-type connection or a lock-type connection.

BACKGROUND

Misconnection collars on both slip- and lock-type syringes have been implemented to avoid wrong-route medication errors. Wrong-route medication errors result from connections between unrelated delivery systems that have different intended uses (e.g. vascular, enteral, respiratory, epidural and intrathecal). The misconnection collars facilitate proper routing of fluids (e.g., medications, enteral feedings) or gases (e.g., oxygen) to a desired route into a patient. International Standard ISO 80369-1:2016(En) is directed to small-bore connectors for liquids and gases in healthcare applications. Small-bore connectors intended to be used for connections in neuraxial applications are to comply with ISO 80369-6. A requirement in ISO 80369-6 (2016), which is incorporated herein by reference, is a 5% taper.

State of the art misconnection collars for slip- and lock-type syringes are visually identical. Glass syringes have opaque collars, unlike many plastic syringes having clear collars, which make it difficult to differentiate by type of connection under busy and/or low light conditions. Plastic syringes may or may not be transparent and therefore it may also be difficult to differentiate plastic syringes by type of connection under busy and/or low light conditions.

There is a need to provide ways to differentiate between components that provide slip-type connections from those that provide lock-type connections.

SUMMARY

Provided are medical devices, specifically syringes, that provide distinguishing visual and tactile features. Methods of distinguishing between devices having slip-type from those having lock-type connections are also provided.

In an aspect, a medical device comprises: a device body having an end; and a connector extending from the end of the device body in fluid communication therewith, wherein an outside surface of the connector includes a visual and tactile feature that is an indicator of a connection-type of the connector.

The connection-type may be defined by an inside surface of the connector. The inside surface may be smooth, the visual and tactile being is one or more grooves or projections that are substantially parallel to a longitudinal axis of the syringe, and the connection-type being a slip-type connection. The inside surface may comprise threads, the visual and tactile feature being one or more grooves or projections that spiral at an angle greater than zero relative to an edge of the end, and the connection-type being a lock-type connection.

The connector may be engagable with one or more of: a needle hub, a filter, and an adapter. The connector may be an opaque material. The connector may comprise a collar disposed coaxially around an elongate tip.

The device body may be a syringe barrel having a distal wall at the end and the connector extends from the distal wall.

Another aspect provides a syringe comprising: a syringe barrel having a distal end, a distal tip, an open proximal end, a barrel sidewall extending between the distal end to the open proximal end and defining a chamber, the distal end of the syringe barrel including a distal wall; a connector extending distally from the syringe barrel at the distal wall and including a visual and tactile feature that is an indicator of a connection-type of the connector.

The connector may comprise a collar disposed coaxially around an elongate tip in fluid communication with the distal dip, a channel formed between the elongate tip and the collar, and an outside surface of the collar including the visual and tactile feature. The connector may be an opaque material.

The connector may comprise a 5% taper. The connector may be compliant with ISO 80369-6 (2016).

In one or more embodiments, the visual and tactile feature is effective to indicate an insertion motion for engaging the connector with one or more of a needle hub, a filter, and an adapter. The visual and tactile feature may be one or more grooves or projections that are substantially parallel to a longitudinal axis of the syringe. The connection-type may be a slip-type connection. The visual and tactile feature maybe one or more grooves or projections that spiral at an angle greater than zero relative to an edge of the distal wall. The connector may comprise one or more internal threads that spiral at an angle greater than zero relative to an edge of the distal wall. The connection-type may be a lock-type connection.

The syringe barrel may be a glass material. The syringe barrel may be a polymeric material.

A further aspect is a syringe comprising: a syringe barrel having a distal end, a distal tip, an open proximal end, a barrel sidewall extending between the distal end to the open proximal end and defining a chamber, the distal end of the syringe barrel including a distal wall; a connector extending distally from the syringe barrel at the distal wall, the connector including a collar disposed coaxially around an elongate tip in fluid communication with the distal tip, a channel formed between the elongate tip and the collar, the collar including an inside surface and an outside surface and a visual and tactile feature on the outside surface of the collar.

The collar may be a metal material and further comprise a syringe collar interface; and the syringe barrel being a glass material and further comprising a distal wall extension to which the syringe collar interface is connected. The collar and the syringe barrel may both be a polymeric material and the collar is integrally formed with the syringe barrel. The collar may comprise a 5% taper. The collar may be compliant with ISO 80369-6 (2016).

In one or more embodiments, the visual and tactile feature is effective to indicate an insertion motion for engaging the connector with one or more of a needle hub, a filter, and an adapter. The visual and tactile feature may be one or more grooves or projections that are substantially parallel to a longitudinal axis of the syringe and the connection-type is a slip-type connection. The visual and tactile feature may be one or more grooves or projections that spiral at an angle greater than zero relative to an edge of the distal wall, the collar comprises one or more threads on the inside surface that spiral at an angle greater than zero relative to an edge of the distal wall, and the connection-type is a lock-type connection.

Another aspect is a method of making a medical device comprises: forming a connector including a visual and tactile feature that is an indicator of a connection-type of the connector; and incorporating the connector in a device body of the medical device.

In an aspects, a method of distinguishing between different connection-type medical devices or syringes comprises: obtaining any the medical device or syringe disclosed herein; and visually and/or tactilely inspecting the visual and tactile feature.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Visual and tactile features are provided on medical devices to provide ways to differentiate between connection types.

One or more embodiments provide a syringe that has a misconnection collar that will enable the syringe meet ISO 80369-6 (2016) misconnection requirements. According to one or more embodiments, the syringe can be utilized for neuraxial applications upon incorporation of the collar with a syringe barrel and it will be compliant to ISO 80369-6 (2016).

The following terms shall have, for the purposes of this application, the respective meanings set forth below.

Reference to "visual and tactile features" means those features that provide indicia by both their appearance, which is discernable by looking at the features, and by their 3-dimensional shape, which is discernable by touch. The visual and tactile features herein provide indicia about the type of connection, e.g., slip-type or lock-type, that is internal to a connector. The visual and tactile features of one or more embodiments indicate an insertion motion for engaging the connector with another component. For example, one or more grooves or projections that are substantially parallel to a longitudinal axis of a medical device indicate a straight, push-on motion. Alternatively, one or more grooves or projections that spiral at an angle greater than zero relative to an edge of a medical device that is perpendicular to its longitudinal axis indicate a turning, twist-on motion.

As used herein the term "connector" is understood to include any structure that is part of a neuraxial device that is capable of making a connection with a secondary neuraxial device. Non-limiting examples of connectors in accordance with the present invention include syringe tips, needleless connectors, male Luer connectors, female Luer connectors, side port valves, y-port valves, port valves, and other similar structures.

"Connection-type" refers to the mechanism by which the connector connects to another medical component. Connection-types include but are not limited to slip-type connections and lock-type connections. Slip-type connections are those that use a nominally linear motion to affix a medical device onto a connector. Lock-type connections are those that use primarily a twisting or turning motion to affix a medical device onto a connector. Other medical components to which connectors are connected include but are not limited to spinal needle assemblies, epidural needle assemblies, combined spinal and epidural (CSE) needle assemblies, fluid filters, adapters of tubing.

Figures 1, 2, 3:
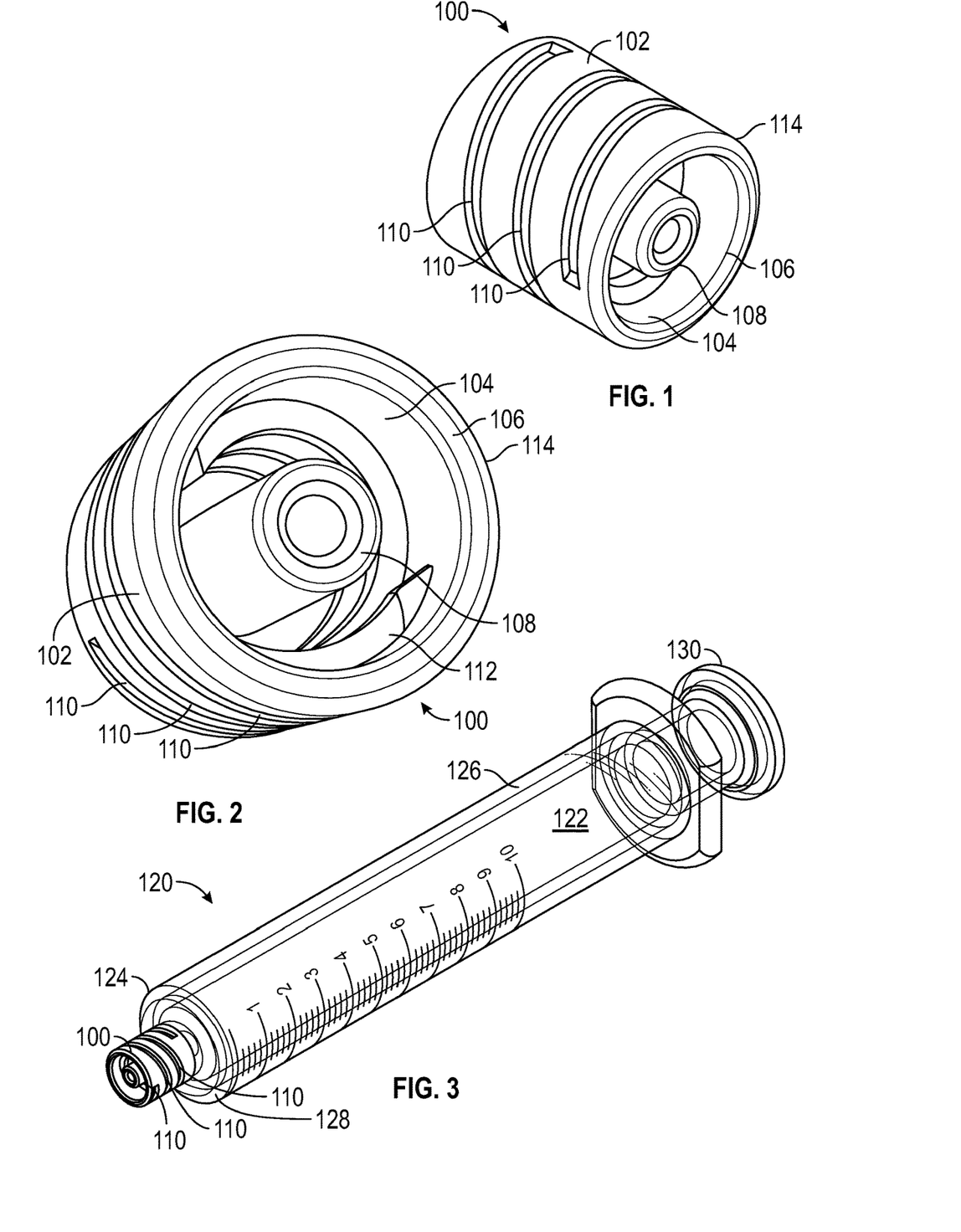
FIGS. 1-2 provide perspective views of a connector having a lock-type connection according to an embodiment.
FIG. 3 is a perspective view of a medical device including the connector of FIGS. 1-2.

In FIGS. 1-2, a connector 100 having an outside surface 102 and an inside surface 104 comprises a collar 106 and an elongate tip 108. On the outside surface 102, there are visual and tactile features 110 that correspond to a connection type, which is defined by the inside surface 104. The inside surface 104 of this embodiment shows threads 112 that are at an angle of greater than zero to an edge 114 of the collar 106. Threads 112 define the connection-type as being a lock-type connection. The treads 112 are engagable with corresponding structures on another medical component such as lugs of a hub of an epidural needle assembly and the like. The motion of connecting to the treads 112 is twist-on. The visual and tactile features 110 comprise grooves that spiral at an angle greater than zero relative to the edge 114. Visually, the grooves follow a curved, twisting shape and tactilely, the touch of a finger will follow the curve of the grooves as an indication that a twisting motion would be needed to assemble the connector 100 with another component in a lock-type connection. While grooves are exemplified in this embodiment, projections could alternatively be used. The visual and tactile features do not contribute structurally to the engagement of the connector and another medical component. Connector 100 is opaque in this embodiment such that the threads 112 cannot be visually detected when viewing the outside surface 102.

FIG. 3 provides a medical device 120 and a connector 100 according to FIGS. 1-2 having the visual and tactile features 110. The device has a device body 122 and an end 124 from which the connector 100 extends. The medical device in this embodiment is a syringe, which comprises a syringe barrel 126, a distal wall 128, and a plunger 130. In one or more embodiments, the medical device is a polymeric material or a plastic and the connector is integrally formed with the device body 122. While the embodiment of FIGS. 1-3 shows an opaque connector 100, it is understood that connectors that are not opaque, e.g., transparent or semi-transparent, will also benefit from the present disclosure, for example, when there are low-lighting environments.

Figures 4, 5, 6:
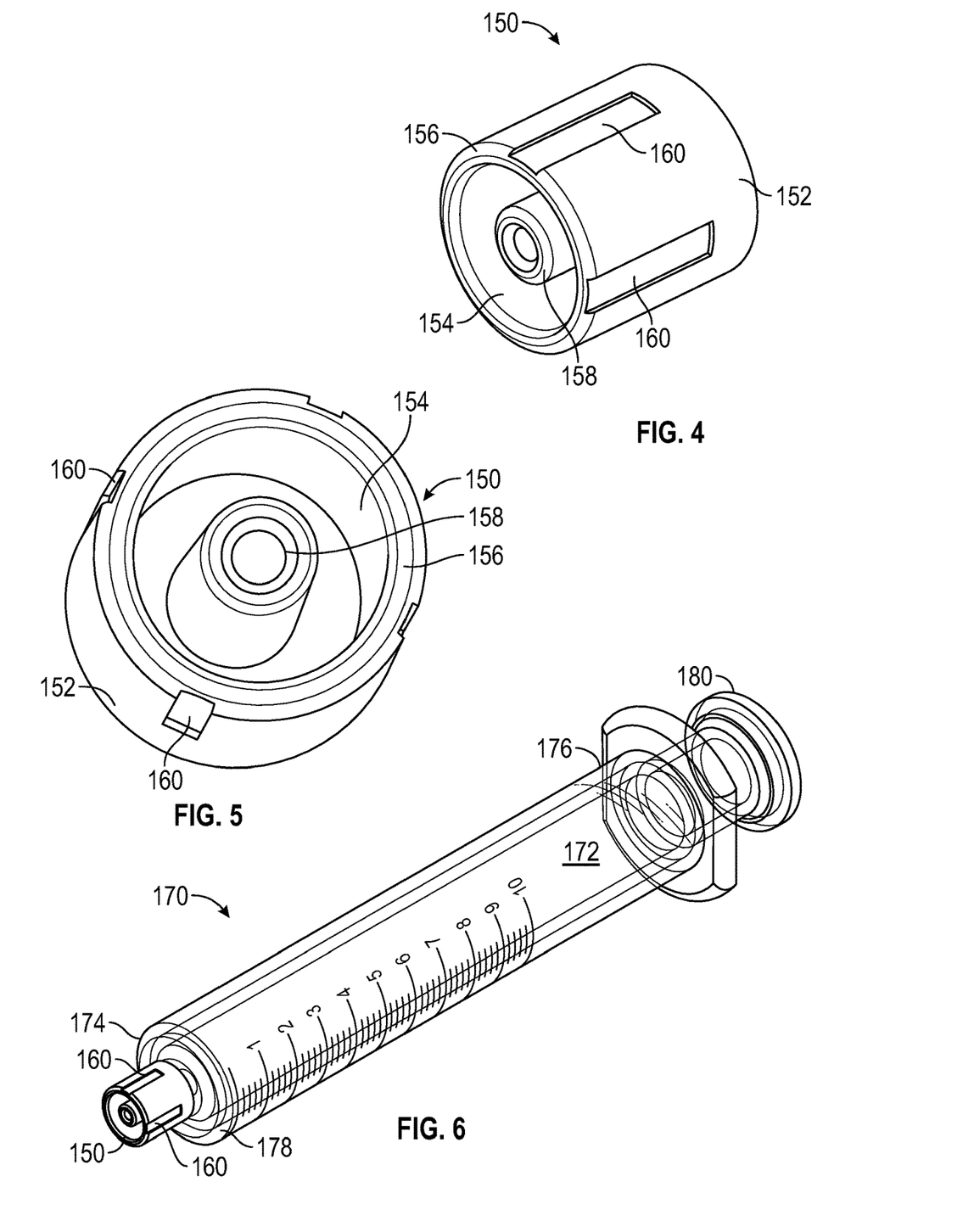
FIGS. 4-5 provide perspective views of a connector having a slip-type connection according to an embodiment.
FIG. 6 is a perspective view of a medical device including the connector of FIGS. 4-5.

In FIGS. 4-5, a connector 150 having an outside surface 152 and an inside surface 154 comprises a collar 156 and an elongate tip 158. On the outside surface 152, there are visual and tactile features 160 that correspond to a connection type, which is defined by the inside surface 154. The inside surface 154 of this embodiment is smooth, which defines the connection-type as being a slip-type connection. The inside surface is engagable with another medical component that fits snugly into a channel formed between the collar 156 and the elongate tip 158, such as a hub of an epidural needle assembly and the like. The motion of connecting to the connector is slip-on. The visual and tactile features 160 comprise grooves that are substantially parallel to a longitudinal axis of the syringe. Visually, the grooves follow a straight shape and tactilely, the touch of a finger will follow the curve of the grooves as an indication that a push-on motion would be needed to assemble the connector 150 with another component in a slip-type connection. While grooves are exemplified in this embodiment, projections could alternatively be used. The visual and tactile features do not contribute structurally to the engagement of the connector and another medical component. Connector 150 is opaque in this embodiment such that the inside surface 154 cannot be visually detected when viewing the outside surface 152.

FIG. 6 provides a medical device 170 and a connector 150 according to FIGS. 4-5 having the visual and tactile features 160. The device has a device body 172 and an end 174 from which the connector 150 extends. The medical device in this embodiment is a syringe, which comprises a syringe barrel 176, a distal wall 178, and a plunger 180. In one or more embodiments, the medical device is a polymeric material or a plastic and the connector is integrally formed with the device body 172. While the embodiment of FIGS. 4-6 shows an opaque connector 150, it is understood that connectors that are not opaque, e.g., transparent or semi-transparent, will also benefit from the present disclosure, for example, when there are low-lighting environments.

Figures 7, 8, 9:
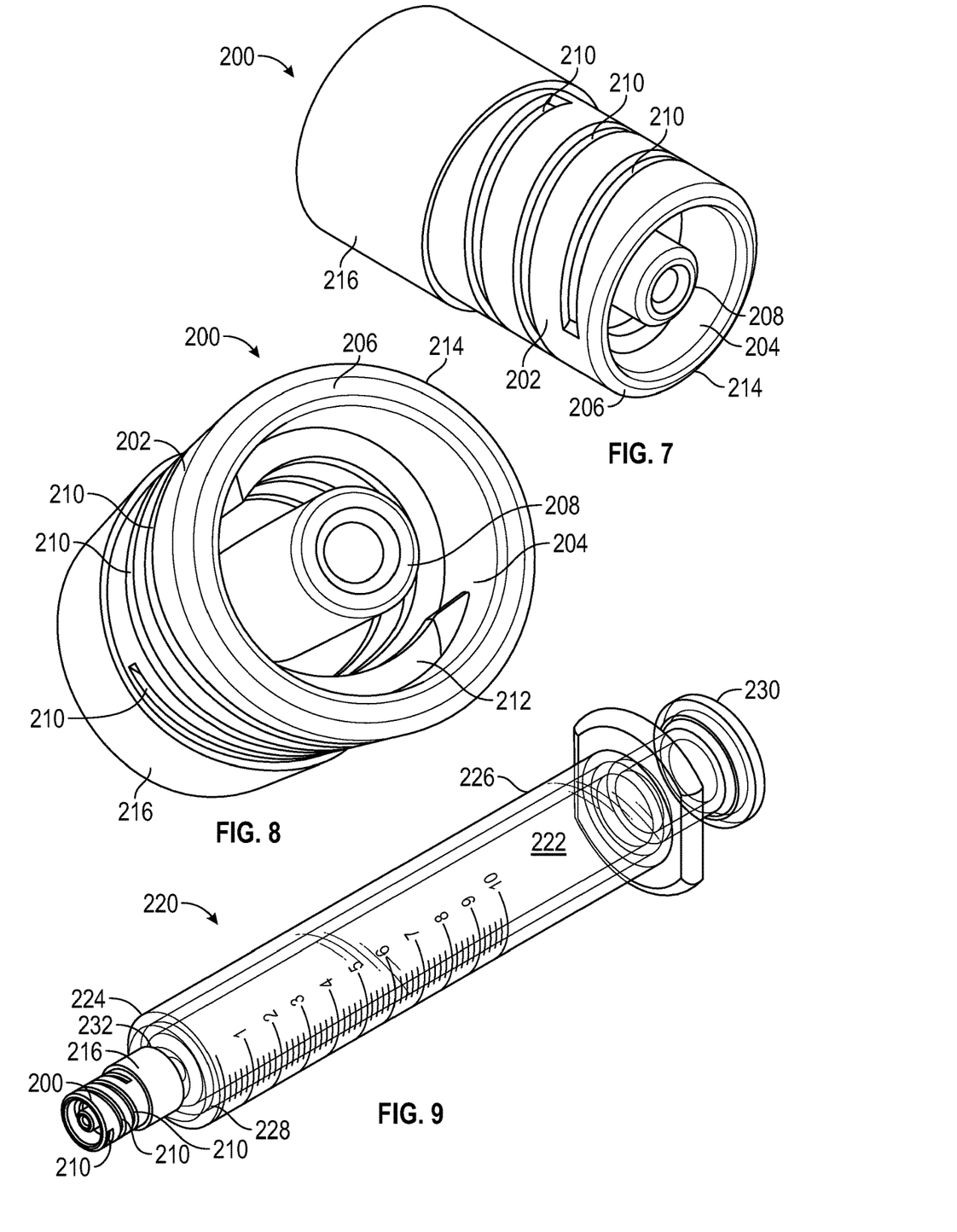
FIGS. 7-8 provide perspective views of a connector having a lock-type connection according to an embodiment.
FIG. 9 is a perspective view of a medical device including the connector of FIGS. 7-8.

In FIGS. 7-8, a connector 200 having an outside surface 202 and an inside surface 204 comprises a collar 206 and an elongate tip 208 and an interface 216. On the outside surface 202, there are visual and tactile features 210 that correspond to a connection type, which is defined by the inside surface 204. The inside surface 204 of this embodiment shows threads 212 that are at an angle of greater than zero to an edge 214 of the collar 206. Threads 212 define the connection-type as being a lock-type connection. The treads 212 are engagable with corresponding structures on another medical component such as lugs of a hub of an epidural needle assembly and the like. The motion of connecting to the treads 212 is twist-on. The visual and tactile features 210 comprise grooves that spiral at an angle greater than zero relative to the edge 214. Visually, the grooves follow a curved, twisting shape and tactilely, the touch of a finger will follow the curve of the grooves as an indication that a twisting motion would be needed to assemble the connector 200 with another component in a lock-type connection. While grooves are exemplified in this embodiment, projections could alternatively be used. The visual and tactile features do not contribute structurally to the engagement of the connector and another medical component. Connector 200 is opaque in this embodiment, e.g., metal, such that the threads 112 cannot be visually detected when viewing the outside surface 102.

FIG. 9 provides a medical device 220 and a connector 200 according to FIGS. 7-8 having the visual and tactile features 210. The device has a device body 222 and an end 224 from which a distal wall extension 232 and the connector 200 extends. The medical device in this embodiment is a syringe, which comprises a syringe barrel 226, a distal wall 228, and a plunger 230. In one or more embodiments, the medical device is glass and the connector 200 is metal being form-fit at a syringe collar interface 216 and the distal wall extension 232. While the embodiment of FIGS. 7-9 shows an opaque connector 200, it is understood that connectors that are not opaque, e.g., transparent or semi-transparent, will also benefit from the present disclosure, for example, when there are low-lighting environments.

Figures 10, 11, 12:
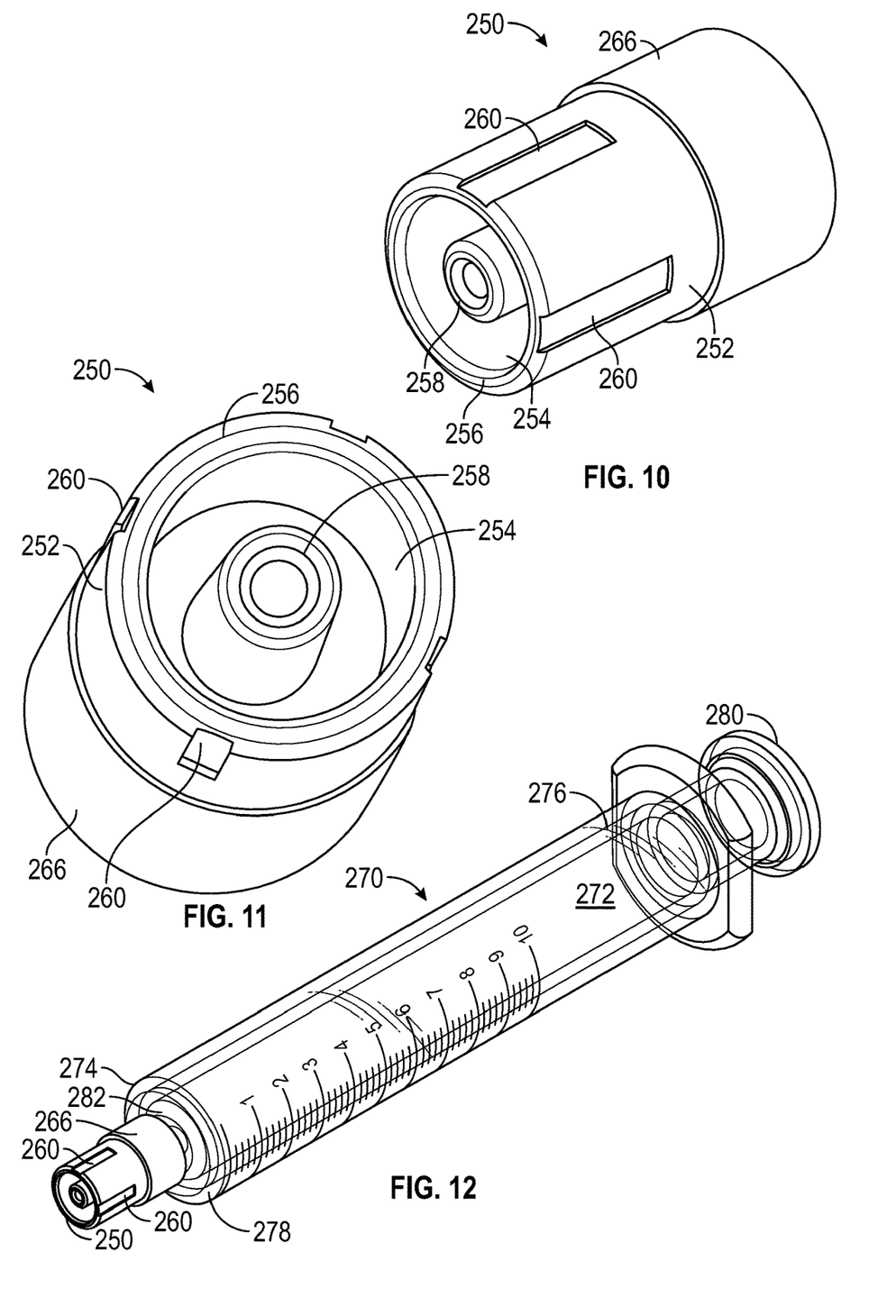
FIGS. 10-11 provide perspective views of a connector having a slip-type connection according to an embodiment.
FIG. 12 is a perspective view of a medical device including the connector of FIGS. 10-11.

In FIGS. 10-11, a connector 250 having an outside surface 252 and an inside surface 254 comprises a collar 256 and an elongate tip 258 and an interface 266. On the outside surface 252, there are visual and tactile features 260 that correspond to a connection type, which is defined by the inside surface 254. The inside surface 254 of this embodiment is smooth, which defines the connection-type as being a slip-type connection. The inside surface is engagable with another medical component that fits snugly into a channel formed between the collar 256 and the elongate tip 258, such as a hub of an epidural needle assembly and the like. The motion of connecting to the connector is slip-on. The visual and tactile features 260 comprise grooves that are substantially parallel to a longitudinal axis of the syringe. Visually, the grooves follow a straight shape and tactilely, the touch of a finger will follow the curve of the grooves as an indication that a push-on motion would be needed to assemble the connector 250 with another component in a slip-type connection. While grooves are exemplified in this embodiment, projections could alternatively be used. The visual and tactile features do not contribute structurally to the engagement of the connector and another medical component. Connector 250 is opaque in this embodiment, e.g., metal, such that the inside surface 254 cannot be visually detected when viewing the outside surface 252.

FIG. 12 provides a medical device 270 and a connector 250 according to FIGS. 10-11 having the visual and tactile features 260. The device has a device body 272 and an end 274 from which the connector 250 extends. The medical device in this embodiment is a syringe, which comprises a syringe barrel 276, a distal wall 278, and a plunger 280. In one or more embodiments, the medical device is glass and the connector 250 is metal being form-fit at a syringe collar interface 266 and the distal wall extension 282. While the embodiment of FIGS. 10-12 shows an opaque connector 250, it is understood that connectors that are not opaque, e.g., transparent or semi-transparent, will also benefit from the present disclosure, for example, when there are low-lighting environments.

Figure 13:
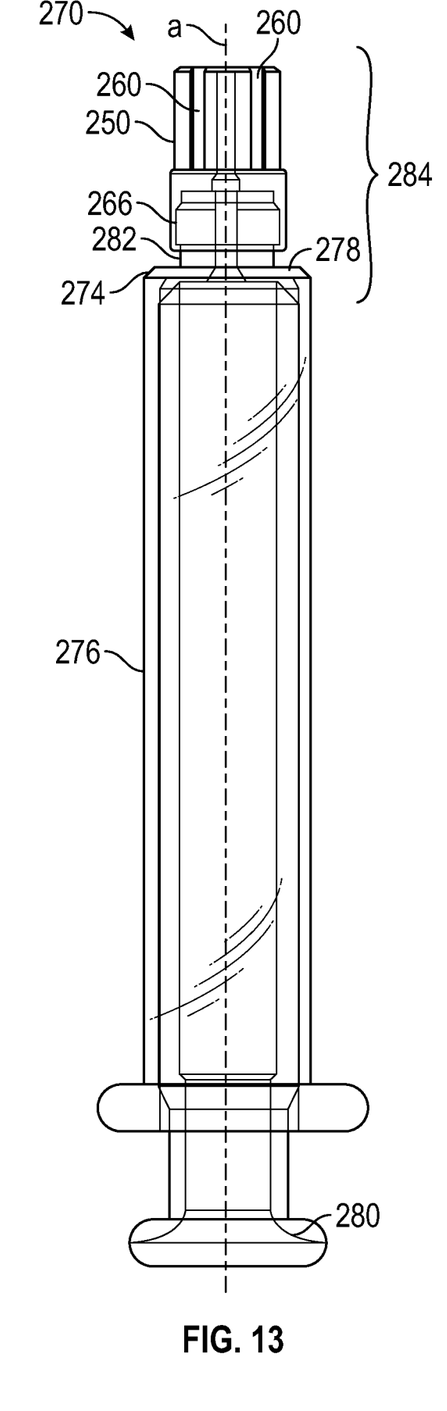
FIG. 13 is a cross-section view of the medical device of FIG. 12.
Figure 14:
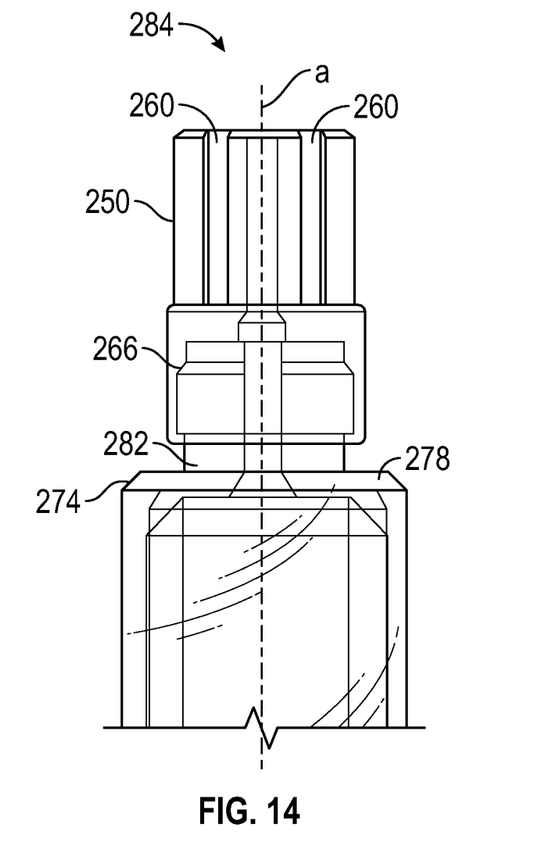
FIG. 14 is a close-up view of the cross-section view of FIG. 13.

FIG. 13 is a cross-section view of the medical device of FIG. 12, and FIG. 14 is a close-up view of connector end 284 of FIG. 13. Longitudinal axis "a" is shown with respect to the medical device 270. The connector 250 according to FIGS. 10-11 has the visual and tactile features 260, which are grooves that are substantially parallel to the longitudinal axis a indicating a straight, push-on motion. The connector 250 form fits to the distal wall extension 282, which extends from the distal wall 278 of the syringe barrel 276, at its syringe collar interface 266. The plunger 280 is in the body of the syringe barrel 276.

Figure 15:
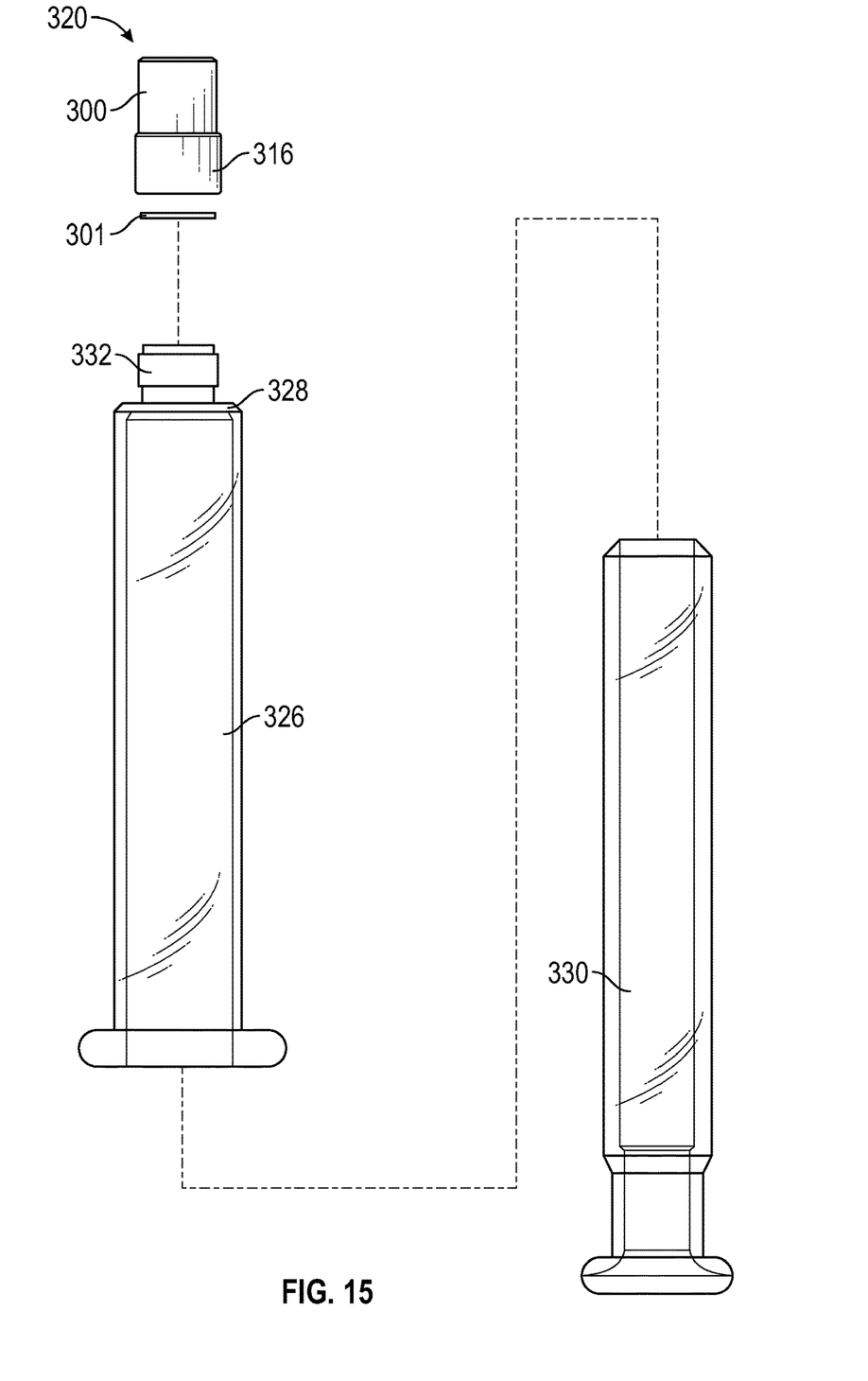
FIG. 15 is an exploded view of an embodiment of a medical device.

FIG. 15 is an exploded view of an embodiment of a medical device in the form of a syringe 320 comprising a connector 300, which can be any embodiment of the present disclosure. A washer 301 is positioned between the connector 300 and a portion of a syringe barrel 326 upon assembly of the syringe 320. In this embodiment, there is a distal wall 328 from which a distal wall extension 332 extends to which a syringe collar interface 316 of the connector 300 is fit. Plunger 330 resides in the syringe barrel 326 upon assembly of the device.

EMBODIMENTS

Various embodiments are listed below. It will be understood that the embodiments listed below may be combined with all aspects and other embodiments in accordance with the scope of the invention.

Embodiment 1

A medical device comprising: a device body having an end; and a connector extending from the end of the device body in fluid communication therewith, wherein an outside surface of the connector includes a visual and tactile feature that is an indicator of a connection-type of the connector.

Embodiment 2

The medical device of embodiment 1, wherein the connection-type is defined by an inside surface of the connector.

Embodiment 3

The medical device of embodiment 1 or 2, wherein the inside surface is smooth, the visual and tactile feature is one or more grooves or projections that are substantially parallel to a longitudinal axis of the syringe, and the connection-type is a slip-type connection.

Embodiment 4

The medical device of embodiment 1 or 2, wherein the inside surface comprises threads, the visual and tactile feature is one or more grooves or projections that spiral at an angle greater than zero relative to an edge of the end, and the connection-type is a lock-type connection.

Embodiment 5

The medical device of one of embodiments 1 to 4, wherein the connector is engagable with one or more of: a needle hub, a filter, and an adapter.

Embodiment 6

The medical device of one of embodiments 1 to 5, wherein the connector is an opaque material.

Embodiment 7

The medical device of one of embodiments 1 to 6, wherein the connector comprises a collar disposed coaxially around an elongate tip.

Embodiment 8

The medical device of one of embodiments 1 to 7, wherein the device body is a syringe barrel having a distal wall at the end and the connector extends from the distal wall.

Embodiment 9

A syringe comprising: a syringe barrel having a distal end, a distal tip, an open proximal end, a barrel sidewall extending between the distal end to the open proximal end and defining a chamber, the distal end of the syringe barrel including a distal wall; a connector extending distally from the syringe barrel at the distal wall and including a visual and tactile feature that is an indicator of a connection-type of the connector.

Embodiment 10

The syringe of embodiment 9, wherein the connector comprises a collar disposed coaxially around an elongate tip in fluid communication with the distal dip, a channel formed between the elongate tip and the collar, and an outside surface of the collar including the visual and tactile feature.

Embodiment 11

The syringe of embodiment 9 or 10, wherein the connector is an opaque material.

Embodiment 12

The syringe of one of embodiments 9 to 11, wherein the connector comprises a 5% taper.

Embodiment 13

The syringe of one of embodiments 9 to 12, wherein the connector is compliant with ISO 80369-6 (2016).

Embodiment 14

The syringe of one of embodiments 9 to 13, wherein the visual and tactile feature is effective to indicate an insertion motion for engaging the connector with one or more of a needle hub, a filter, and an adapter.

Embodiment 15

The syringe of one of embodiments 9 to 14, wherein the visual and tactile feature is one or more grooves or projections that are substantially parallel to a longitudinal axis of the syringe.

Embodiment 16

The syringe of embodiment 15, wherein the connection-type is a slip-type connection.

Embodiment 17

The syringe of one of embodiments 9 to 14, wherein the visual and tactile feature is one or more grooves or projections that spiral at an angle greater than zero relative to an edge of the distal wall.

Embodiment 18

The syringe of one of embodiments 9 to 14 or 17, wherein the connector comprises one or more internal threads that spiral at an angle greater than zero relative to an edge of the distal wall.

Embodiment 19

The syringe of embodiment 18, wherein the connection-type is a lock-type connection.

Embodiment 20

The syringe of one of embodiments 9 to 19, wherein the syringe barrel is a glass material.

Embodiment 21

The syringe of one of embodiments 9 to 19, wherein the syringe barrel is a polymeric material.

Embodiment 22

A syringe comprising: a syringe barrel having a distal end, a distal tip, an open proximal end, a barrel sidewall extending between the distal end to the open proximal end and defining a chamber, the distal end of the syringe barrel including a distal wall; a connector extending distally from the syringe barrel at the distal wall, the connector including a collar disposed coaxially around an elongate tip in fluid communication with the distal tip, a channel formed between the elongate tip and the collar, the collar including an inside surface and an outside surface and a visual and tactile feature on the outside surface of the collar.

Embodiment 23

The syringe of embodiment 22, wherein the collar is a metal material and further comprises a syringe collar interface; and the syringe barrel is a glass material and further comprises a distal wall extension to which the syringe collar interface is connected.

Embodiment 24

The syringe of embodiment 22, wherein the collar and the syringe barrel are both a polymeric material and the collar is integrally formed with the syringe barrel.

Embodiment 25

The syringe of one of embodiments 22 to 24, wherein the collar comprises a 5% taper.

Embodiment 26

The syringe of one of embodiments 22 to 25, wherein the collar is compliant with ISO 80369-6 (2016).

Embodiment 27

The syringe of one of embodiments 22 to 26, wherein the visual and tactile feature is effective to indicate an insertion motion for engaging the connector with one or more of a needle hub, a filter, and an adapter.

Embodiment 28

The syringe of one of embodiments 22 to 27, wherein the visual and tactile feature is one or more grooves or projections that are substantially parallel to a longitudinal axis of the syringe and the connection-type is a slip-type connection.

Embodiment 29

The syringe of one of embodiments 22 to 27, wherein the visual and tactile feature is one or more grooves or projections that spiral at an angle greater than zero relative to an edge of the distal wall, the collar comprises one or more threads on the inside surface that spiral at an angle greater than zero relative to an edge of the distal wall, and the connection-type is a lock-type connection.

Embodiment 30

A method of making a medical device comprising: forming a connector including a visual and tactile feature that is an indicator of a connection-type of the connector; and incorporating the connector in a device body of the medical device.

Embodiment 31

A method of distinguishing between different connection-type medical devices or syringes comprising: obtaining the medical device or syringe according to one of embodiments 1 to 29; and visually and/or tactilely inspecting the visual and tactile feature.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical device comprising:
    a device body, having an end; and
    a connector extending from the end of the device body in fluid communication therewith, wherein an outside surface of the connector includes a visual and tactile feature that is an indicator of a connection-type of the connector to a secondary component, the visual and tactile feature having a 3-dimensional shape that indicates an insertion motion for engaging the connector with the secondary component, and the connection-type being defined by an inside surface of the connector;
    wherein the inside surface comprises threads, the visual and tactile feature is one or more grooves or projections relative to the outside surface of the connector that spiral at an angle greater than zero relative to an edge of the end, and the connection-type is a lock-type connection.

2. The medical device of claim 1, wherein the connector is engagable with one or more of: a needle hub, a filter, and an adapter.

3. The medical device of claim 1, wherein the connector comprises an opaque material.

4. The medical device of claim 1, wherein the connector comprises a collar disposed coaxially around an elongate tip.

5. The medical device of claim 1, wherein the device body is a syringe barrel having a distal wall at the end and the connector extends from the distal wall.

6. A method of distinguishing between different connection-type medical devices comprising:
obtaining the medical device according to claim 1; and
visually and/or tactilely inspecting the visual and tactile feature.

7. A syringe comprising:
a syringe barrel having a distal end, a distal tip, an open proximal end, a barrel sidewall extending between the distal end to the open proximal end and defining a chamber, the distal end of the syringe barrel including a distal wall;
a connector extending distally from the syringe barrel at the distal wall and including a visual and tactile feature on an outside surface of the connector that is an indicator of a connection-type of the connector to a secondary component, the visual and tactile feature having a 3-dimensional shape that indicates an insertion motion for engaging the connector with the secondary component, and the connection-type being defined by an inside surface of the connector and being a lock-type connection;
wherein the visual and tactile feature is one or more grooves or projections relative to the outside surface of the connector that spiral at an angle greater than zero relative to an edge of the distal wall.

8. The syringe of claim 7, wherein the connector comprises a collar disposed coaxially around an elongate tip in fluid communication with the distal tip, a channel formed between the elongate tip and the collar, and an outside surface of the collar including the visual and tactile feature.

9. The syringe of claim 7, wherein the connector comprises an opaque material.

10. The syringe of claim 7, wherein the connector comprises a 5% taper.

11. The syringe of claim 7, wherein the connector is compliant with ISO 80369-6 (2016).

12. The syringe of claim 7, wherein the visual and tactile feature is effective to indicate an insertion motion for engaging the connector with one or more of a needle hub, a filter, and an adapter.

13. The syringe of claim 7, wherein the connector comprises one or more internal threads that spiral at an angle greater than zero relative to the edge of the distal wall.

14. The syringe of claim 7, wherein the syringe barrel comprises a glass material.

15. The syringe of claim 7, wherein the syringe barrel comprises a polymeric material.

16. A syringe comprising:
a syringe barrel having a distal end, a distal tip, an open proximal end, a barrel sidewall extending between the distal end to the open proximal end and defining a chamber, the distal end of the syringe barrel including a distal wall;
a connector extending distally from the syringe barrel at the distal wall, the connector including a collar disposed coaxially around an elongate tip in fluid communication with the distal tip, a channel formed between the elongate tip and the collar, the collar including an inside surface, an outside surface, and a visual and tactile feature on the outside surface of the collar, the visual and tactile feature being an indicator of a connection-type of the connector to a secondary component and having a 3-dimensional shape that indicates an insertion motion for engaging the connector with the secondary component, and the connection-type being defined by the inside surface of the collar and being a lock-type connection;
wherein the visual and tactile feature is one or more grooves or projections, which are indicators of the lock-type connection, relative to the outside surface of the collar that spiral at an angle greater than zero relative to an edge of the distal wall, and the collar comprises one or more threads on the inside surface that spiral at an angle greater than zero relative to the edge of the distal wall.

17. The syringe of claim 16, wherein the collar comprises a metal material and further comprises a syringe collar interface; and the syringe barrel comprises a glass material and further comprises a distal wall extension to which the syringe collar interface is connected.

18. The syringe of claim 16, wherein the collar and the syringe barrel both comprise a polymeric material and the collar is integrally formed with the syringe barrel.

19. The syringe of claim 16, wherein the collar comprises a 5% taper.

20. The syringe of claim 16, wherein the collar is compliant with ISO 80369-6 (2016).

21. The syringe of claim 16, wherein the visual and tactile feature is effective to indicate an insertion motion for engaging the connector with one or more of a needle hub, a filter, and an adapter.

22. A method of making a medical device comprising:
forming a connector including a visual and tactile feature on an outside surface of the connector, the visual and tactile feature being an indicator of a connection-type of the connector to a secondary component and having a 3-dimensional shape that indicates an insertion motion for engaging the connector with the secondary component, and the connection-type being defined by an inside surface of the connector; and
incorporating the connector in a device body of the medical device, the device body comprising a distal wall;
wherein the visual and tactile feature is one or more grooves or projections relative to the outside surface of the connector that spiral at an angle greater than zero relative to an edge of the distal wall and which are indicators of the lock-type connection, the inside surface comprising one or more threads that spiral at an angle greater than zero relative to the edge of the distal wall.

* * * * *

UNITED STATES PATENT AND TRADEMARK OFFICE
CERTIFICATE OF CORRECTION

| | | |
|---|---|---|
| PATENT NO. | : 10,857,343 B2 | Page 1 of 1 |
| APPLICATION NO. | : 15/480903 | |
| DATED | : December 8, 2020 | |
| INVENTOR(S) | : John Di Ubaldi et al. | |

It is certified that error appears in the above-identified patent and that said Letters Patent is hereby corrected as shown below:

On the Title Page

Page 2, Item (56), Column 1, under "References Cited – U.S. PATENT DOCUMENTS", Line 3, replace "6,702,769" with "6,702,789".

In the Claims

Column 10, Claim 1, Line 48, replace "body, having" with "body having".

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*